(12) United States Patent
Baruch et al.

(10) Patent No.: US 9,012,221 B2
(45) Date of Patent: Apr. 21, 2015

(54) METHOD FOR PRODUCING PLATELETS FROM MEGAKARYOCYTES

(75) Inventors: Dominique Baruch, Paris Cedex (FR); Elisabeth Cramer-Borde, Boulogne (FR); Claire Dunois, Paris Cedex (FR)

(73) Assignees: INSERM (Institut National de la Sante et de la Recherche Medicale), Paris (FR); Universite Paris Descartes, Paris (FR); Assistance Publique Hopitaux de Paris, Paris (FR); Universite de Versailles Saint-Quentin-en-Yvelines, Versailles (FR)

( * ) Notice: Subject to any disclaimer, the term of this patent is extended or adjusted under 35 U.S.C. 154(b) by 989 days.

(21) Appl. No.: 13/132,527

(22) PCT Filed: Dec. 4, 2009

(86) PCT No.: PCT/EP2009/066401
§ 371 (c)(1),
(2), (4) Date: Sep. 22, 2011

(87) PCT Pub. No.: WO2010/063823
PCT Pub. Date: Jun. 10, 2010

(65) Prior Publication Data
US 2012/0014933 A1    Jan. 19, 2012

(30) Foreign Application Priority Data
Dec. 4, 2008 (EP) .................... 08305881

(51) Int. Cl.
*C12N 5/078* (2010.01)
*A61K 35/12* (2006.01)

(52) U.S. Cl.
CPC ......... *C12N 5/0644* (2013.01); *A61K 2035/124* (2013.01); *C12N 2501/125* (2013.01); *C12N 2501/145* (2013.01); *C12N 2521/00* (2013.01); *C12N 2533/50* (2013.01)

(58) Field of Classification Search
CPC ............. C12N 2521/00; C12N 5/0644; A61K 2035/124; A61K 35/19
See application file for complete search history.

(56) References Cited

U.S. PATENT DOCUMENTS 4,344,560 A * 8/1982 Iriguchi et al. .................. 494/10

FOREIGN PATENT DOCUMENTS

WO    01/38495    5/2001

OTHER PUBLICATIONS

Balduini et al., J. Thromb. Haemost., 6(11):1900-1907 (2008).
Briede et al., J. Thromb. Haemost., 1(3):559-565 (2003).
Conant et al., "Platelet adhesion and aggregation under flow using microfluidic flow cells." Journal of Visualized Experiments [Online] http://www.jove.com/index/Details.stp?ID=1644 (2009) XP002563897.
Dunois-Larde et al., Blood, 114(9):1875-1883 (2009).
Eldor et al., Blood Cells, 17(3):447-463 (1991).
European Search Report in EP 08305881, dated Jun. 22, 2009.
International Search Report in PCT/EP2009/066401, dated Feb. 1, 2010.
Italiano et al., J. Thromb. Haemost., 1:1174-1182 (2003).
Kauskot et al., J. Biol. Chem., 282(44):31990-31999 (2007).
Keuren et al., Blood, 103(5):1741-1746 (2004).
Legendre et al., J. Thromb. Haemost., 4(1):236-246 (2006).
Mekrache et al., Br. J. Haematol., 119(4):1024-1032 (2002).
Williams et al., JALA, 7(6):135-141 (2002).
Junt et al., "Dynamic visualization of thrombopoiesis within bone marrow," Science, 317:1767-1770 (2007) with supporting online material.

* cited by examiner

*Primary Examiner* — Sandra Saucier
(74) *Attorney, Agent, or Firm* — McAndrews, Held & Malloy Ltd.

(57) ABSTRACT

The present invention relates to a method for producing platelets from mature megakaryocytes. More particularly, the invention relates to an ex vivo method for producing platelets, from mature megakaryocytes, said method comprising a step of subjecting a suspension of mature megakaryocytes to a flow having a minimal shear rate of 600 $s^{-1}$ on a solid phase coated with Von Willebrand factor.

5 Claims, 9 Drawing Sheets

METHOD FOR PRODUCING PLATELETS FROM MEGAKARYOCYTES

Figure 1A:
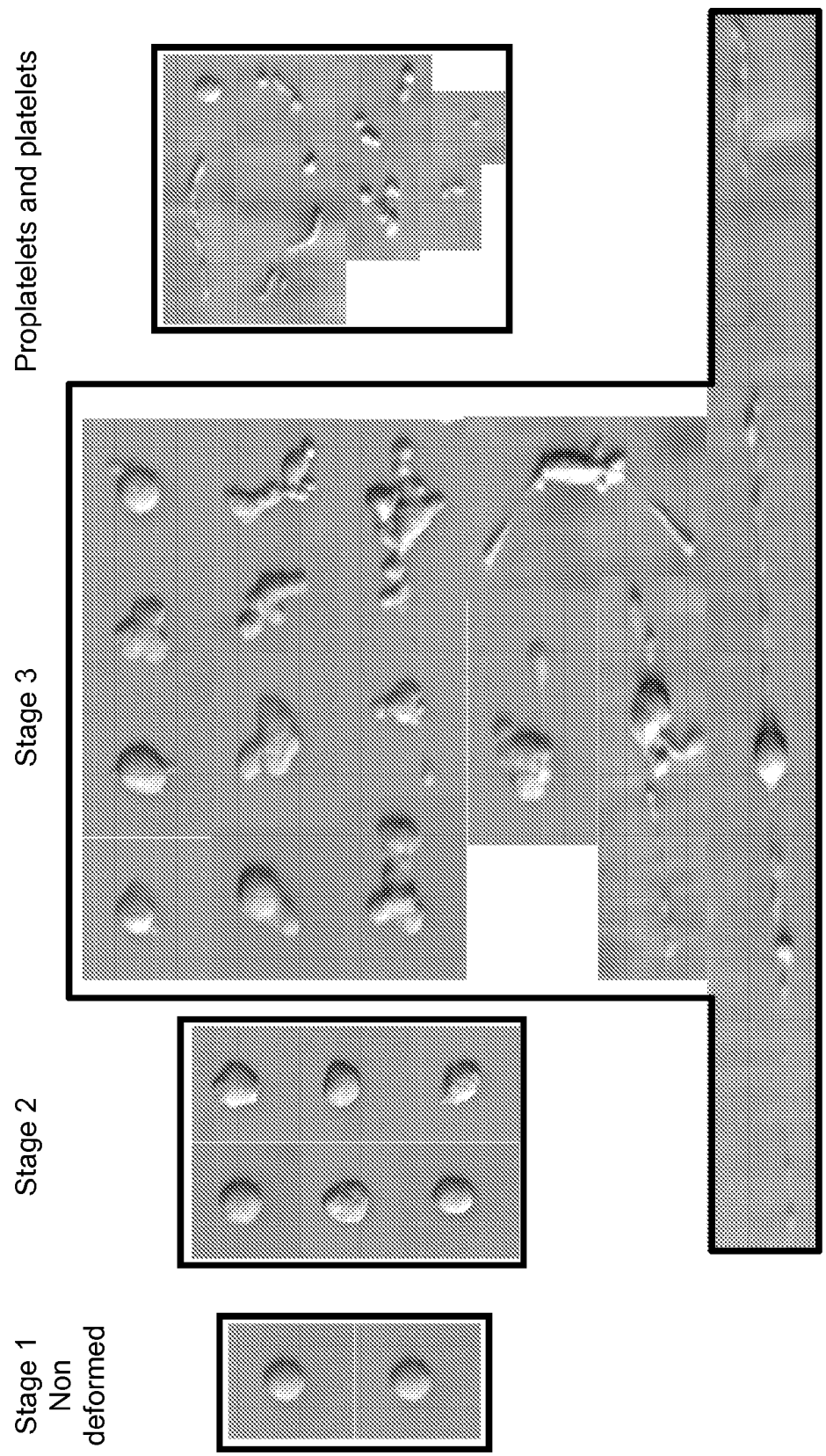

The present application is filed pursuant to 35 U.S.C. 371 as a U.S. National Phase application of International Patent Application No. PCT/EP2009/066401, which was filed Dec. 4, 2009, claiming the benefit of priority to European Patent Application No. 08305881.8, which was filed on Dec. 4, 2008. The entire text of the aforementioned applications is incorporated herein by reference in its entirety.

FIELD OF THE INVENTION

The present invention relates to a method for producing platelets from mature megakaryocytes.

BACKGROUND OF THE INVENTION

Megakaryocyte (MK) differentiation is a continuous process characterized by sequential steps. MK ploidy increases through endomitosis, with a parallel increase in cell size. Synthesis of storage organelles and plasma membrane is enhanced, resulting in the formation of demarcation membranes. Cytoplasmic maturation is associated with a marked increase in MK size. Finally, mature MK undergo complete cytoskeleton reorganization with microtubule involvement, to induce pseudopodial elongations corresponding to proplatelets (Patel et al., 2005a; Richardson et al., 2005). Platelets are released from the tips of these proplatelets that contain all the platelet organelles.

Circulating platelets are involved in thrombus formation by adhesion to the vessel wall and by aggregation on the first layer of adherent platelets to the subendothelial matrix (Ruggeri, 2003). Von Willebrand factor (VWF) is a major constituent of endothelial cells lining the vasculature. VWF is the only protein able to arrest circulating platelets in conditions of high shear rates (>1000 $s^{-1}$). Tethered platelets translocate on immobilized matrix VWF, through the binding of GPIb (also known as CD42b) to VWF A1 domain (Huizinga et al., 2002). Activation of the $\alpha IIb\beta 3$ integrin (also known as CD41a/CD61), that occurs progressively during transient tethering of platelets, involves GPIb-mediated signalling and allows $\alpha IIb\beta 3$ binding to the RGD sequence of VWF. The Bernard-Soulier Syndrome (BSS) is a bleeding disorder characterized by severe thrombocytopenia and giant platelets (Nurden, 2005). It is due to quantitative or qualitative abnormalities of the GPIb-IX-V complex, in particular of the GPIbα subunit that contains the VWF binding site. Normal numbers of MKs are found in the bone marrow of BSS patients, suggesting that the macrothrombocytopenia observed in this setting is related to defective platelet formation from MKs.

Since MK fragmentation into platelets is not often observed in the marrow space, MKs need to migrate into the bone marrow capillaries (Tavassoli and Aoki, 1981). Platelet detachment from proplatelets has been described in the absence of flow conditions. It is intriguing that the yield of platelets shed from cultured MKs in the presence of thrombopoietin (TPO) is far below what could be expected in optimal maturation conditions (Norol et al., 1998). Many steps of platelet shedding remain elusive. In particular a role of shear forces on platelet formation has never been demonstrated. The VWF receptors GPIb and $\alpha IIb\beta 63$ are both expressed on the MK surface during maturation (Debili et al., 1990). Few mature MKs have been identified in the blood circulation (Pedersen, 1978; Tavassoli and Aoki, 1981), where they are exposed to VWF on the luminal side of endothelial cells.

Moreover, it is intriguing that in optimal MK culture conditions, the yield of shed platelets in vitro is far below what could be expected from the large daily platelet production in vivo. So, there is an important need of a good system of platelet production.

SUMMARY OF THE INVENTION

The invention relates to an ex vivo method for producing platelets, from mature megakaryocytes, said method comprising a step of subjecting a suspension of mature megakaryocytes to a flow having a shear rate of at least 600 $s^{-1}$ on a solid phase coated with Von Willebrand factor.

DETAILED DESCRIPTION OF THE INVENTION

Definitions

As used herein, the term "platelets" denotes the anucleated cytoplasmic bodies derived from cells that are involved in the cellular mechanisms of primary hemostasis leading to the formation of blood clots.

As used herein, the term "Proplatelets" denotes any structural form of a megakaryocyte or its fragments, such as cytoplasmically-linked platelet-like particles, that could result in platelet formation. The structural forms include, but are not limited to, cells with long cytoplasmic extensions, projections or pseudopodia that contain swellings encompassing platelet bodies in various stages of formation, such as, nodules, blebs, and the like.

As used herein, the term "megakaryocyte" denotes a bone marrow cell responsible for the production of blood platelets necessary for normal hemostasis. Megakaryocytes are derived from hematopoietic stem cell precursor cells in the bone marrow. The primary signal for megakaryocyte production is thrombopoietin or TPO. TPO is necessary for inducing differentiation of progenitor cells in the bone marrow towards a final megakaryocyte phenotype. Other molecular signals for megakaryocyte differentiation include GM-CSF, IL-3, IL-6, IL-11, and erythropoietin.

As used herein, the term "mature megakaryocytes" denotes a population of megakaryocytes which express in a stable way GPIb and $\alpha IIb\beta 3$ surface markers. As used herein, a "stable way expression" of a surface marker denotes that in a cellular population, at least 70% of cells express these surface markers.

As used herein, the term "shear rate" refers to the parameter used to characterize laminar flow. In tubes laminar flow has a parabolic flow velocity profile with increasing flow velocity of the adjacent streaming layers reaching a maximum at the luminal axis. The rate of radial velocity increase in adjacent layers is defined as the shear rate. In a parallel-plate chamber the shear rate is given by the formula ($\gamma$) and corresponds to a gradient of velocity in a flowing material. The SI unit of measurement for shear rate is $s^{-1}$, expressed as "reciprocal seconds" or "inverse seconds." The formula of the shear rate ($\gamma$) is:

$$\gamma = f(k)\, 6Q/ab^2$$

wherein $\gamma$ is the shear rate (in $s^{-1}$), Q is the flow rate (ml/s), a=slit width (cm), b=slit height (cm) and f(k) is a function of the physical parameters of the system. For example, using a flow chamber from Maastricht Instrumentation (described in (Legendre et al., 2006)), f(k) is equal to 1.03 for shear rates>100 $s^{-1}$. So, the shear rate may be adjusted by controlling the flow rate and the slit height of the chamber.

In the human circulation the shear rates vary from 30-40 s$^{-1}$ in the largest veins to 5000 s$^{-1}$ in the microcirculation.

As used herein, the term "Von Willebrand factor" or "VWF" denotes the multimeric protein consisting of several monomers involved in hemostasis. An exemplary amino acid sequence of human Von Willebrand factor can be found in the GenPept database under accession number AAB59458. Preferably the Von Willebrand factor according to the invention is a mammalian Von Willebrand factor, even more preferably a murine factor or a primate factor, even more preferably human Von Willebrand factor. The term "VWF" encompasses VWF of any mammalian origin, such as primate VWF, preferably human VWF. It can also be recombinant VWF. The skilled person can easily produce recombinant VWF according to standard techniques in the art.

According to the invention, the VWF factor can be recombinant VWF or native VWF. In its native form, it can be purified or can be comprised in a composition comprising other components (e.g. in an extracellular matrix).

Also covered are fragments of VWF, variants of VWF and VWF analogues, wherein said fragments, variants and analogues have the capacity to bind to GPIb. Fragments, variants, and analogues of VWF can include, but are not limited to: the 52/48-kDa tryptic fragment of VWF (Fujimura et al., 1986); *Staphylococcus aureus* V-8 protease-digested VWF (Girma et al., 1986a; Girma et al., 1986); VWF concentrates for therapeutic use (Federici, 2005; Goudemand et al., 2005; Houdijk et al., 1986) such as Haemate-P/Humate-P (from Behring), Wilfactin (from LFB; see (Goudemand et al., 2005)) and Immunate (Baxter, Vienna, Austria); and VWF mutants responsible for type 2N von Willebrand disease (which are deficient in factor VIII binding).

As used herein, the term "decreased platelet count disorder" denotes a problem in the production of platelets or an increased degradation of platelets that result in a low concentration of platelets or a problem due to an abnormal function of platelets which are in the normal range. As used herein a "low concentration of platelets" denotes a concentration lower than 150 000 platelets per mm$^3$. According to the invention, decreased platelet count disorders include but are not limited to auto-immune thrombocytopenia, thrombocytopenia related to decreased production (central origin) and increased destruction of any cause (peripheral origin).

As used herein, the term "subject" denotes a mammal, such as a rodent, a feline, a canine, and a primate. Preferably a subject according to the invention is a human.

Method and Device for Producing Platelets

The invention relates to an ex vivo method for producing platelets comprising a step of subjecting a suspension of mature megakaryocytes to a flow having a shear rate of at least 600 s$^{-1}$ on a solid phase coated with Von Willebrand factor.

In a preferred embodiment, the flow has a shear rate of at least 800 s$^{-1}$, preferably at least 1000 s$^{-1}$, preferably at least 1200 s$^{-1}$, preferably at least 1400 s$^{-1}$, even more preferably at least 1600 s$^{-1}$, at least 1800 s$^{-1}$ or at least 2000 s$^{-1}$.

Typically, the flow has a shear rate which does not exceed the physiological shear rate to which platelets can be submitted in vivo. Typically, said shear rate does not exceed 6000 s$^{-1}$, preferably 4000 s$^{-1}$, even more preferably 3000 s$^{-1}$.

In one embodiment, the suspension of mature megakaryocytes presents a cell concentration comprised between 0.5×10$^6$ and 4×10$^6$ per mL, preferably at least 1×10$^6$ per mL preferably at least 2×10$^6$ cells per mL, even more preferably at least 4×10$^6$ per mL.

Typically, the suspension of mature megakaryocytes comprises a population of megakaryocytes suspended in an appropriate cell culture medium. In one embodiment, said cell culture medium is Iscove's Modified Dulbecco's Medium (IMDM).

The suspension of mature megakaryocytes can be obtained after isolation from a blood sample or bone marrow sample. Alternatively, a suspension of stable megakaryocytic cell lines such as DAMI (Greenberg et al., 1988), Meg-01 (Isakari et al., 2009), UT7/TPO (Barroga et al., 2008) can be used in appropriate conditions. According to the invention, the suspension of mature megakaryocytes is subjected to a shear rate of at least 600 s$^{-1}$ for an exposure time sufficient for the production of platelets. Typically, said exposure time can be comprised between 10 minutes and 2 hours, typically, between 15 minutes to 1 hour, even more preferably between 15 minutes and 30 minutes. In a preferred embodiment, said exposure time is approximately 20 minutes.

In a particular embodiment, the solid phase is coated by incubation with a solution of Von Willebrand factor or fragment or variant or analogue thereof.

Typically the concentration of VWF used for coating the solid phase is between 5 and 100 μg/mL. In a preferred embodiment, the concentration of VWF is 20 μg/mL.

In one embodiment, the solid phase is coated with a fragment or variant or analogue selected from the group consisting of the 52/48-kDa tryptic fragment of VWF; *Staphylococcus aureus* V-8 protease-digested VWF; VWF concentrates for therapeutic use and recombinant wild-type VWF or VWF mutants responsible for type 2N von Willebrand disease.

The method for producing the platelets from mature megakaryocytes may be performed in a flow chamber, wherein the flow chamber comprises a bottom wall coated with VWF or a fragment or variant or analogue thereof, wherein said fragment, variant or analogue thereof binds to GPIb.

The invention also relates to a device for producing the platelets from mature megakaryocytes, said device comprising a flow chamber comprising a bottom wall coated with VWF or a fragment or variant or analogue thereof wherein said fragment, variant or analogue thereof binds to GPIb.

In a preferred embodiment the flow chamber consists of a rectangular cavity.

In a further embodiment, the bottom of the flow chamber is a glass coverslip coated with the factor according to the invention.

In a further embodiment, the flow chamber used for the platelets production may be the chamber described in (Mekrache et al., 2002) and (Legendre et al., 2006).

In another embodiment, the flow chamber is a microfluidic flow system such as glass microcapillary tubes (Kauskot et al., 2007), or a microfluidic biochip and flow sensor (Robinson et al., 2008; Williams et al., 2002), or any other type of microfluidic flow system (see for example Conant et al., 2009).

Advantageously, some of the flow chamber suitable for the invention allow to work under sterile conditions (see Williams et al., 2002 and Conant et al., 2009 for instance). In a preferred embodiment, said flow chamber is sterile.

In a further embodiment, the shear rate is obtained thanks to an electric pump in the flow chamber.

Platelets and Pharmaceutical Compositions

In another object, the invention relates to platelets obtainable by the method as above described.

In a further object of the invention, the platelets obtainable by the method described may be used for the preparation of a pharmaceutical composition.

Hence, the present invention also provides a pharmaceutical composition comprising the platelets according to the invention. The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e. g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Moreover, platelets according to the invention and pharmaceutical compositions according to the invention may be used for the treatment of decreased platelet count disorders, in particular thrombocytopenia and thrombocytopathy. For example, the platelets obtainable by the method according to the invention may be transfused in an efficient amount to a subject suffering of a disorder of platelet production.

In a preferred embodiment, the decreased platelet count disorder may be selected from the group consisting of autoimmune thrombocytopenia, thrombocytopenia related to decreased production (central origin) or increased destruction of any cause (peripheral origin).

A related aspect of the invention relates to a method for treating a subject suffering from a decreased platelet count disorder, said method comprising a step of administering to the subject an efficient amount of platelets according to the invention (or a population thereof or a pharmaceutical composition thereof).

In the context of the invention, the term "treating" or "treatment", as used herein, refers to a method that is aimed at delaying or preventing the onset of a pathology, at reversing, alleviating, inhibiting, slowing down or stopping the progression, aggravation or deterioration of the symptoms of the pathology, at bringing about ameliorations of the symptoms of the pathology, and/or at curing the pathology.

As used herein, the term "efficient amount" refers to any amount of platelets according to the invention (or a population thereof or a pharmaceutical composition thereof) that is sufficient to achieve the intended purpose.

Effective dosages and administration regimens can be readily determined by good medical practice based on the nature of the pathology of the subject, and will depend on a number of factors including, but not limited to, the extent of the symptoms of the pathology and extent of damage or degeneration of the tissue or organ of interest, and characteristics of the subject (e.g., age, body weight, gender, general health, and the like).

For therapy, platelets and pharmaceutical compositions according to the invention may be administered systemically, by intravenous administration. The dose and the number of administrations can be optimized by those skilled in the art in a known manner.

Moreover, platelets according to the invention may be used for diagnostic purposes. They can be used as a normal control for the standardization of platelet function.

Platelet function testing requires fresh blood platelets in native functional condition from normal individuals and affected individuals. Von Willebrand disease is the most common single cause of bleeding disorder. In addition, up to 50% mucocutaneous bleeding disorders are caused by a platelet function disorder. Standardization of platelet function testing requires that the laboratory should perform a normal control with every batch of platelet function tests performed. However continuous regular blood sampling by venipuncture raises several health concerns and ethical issues. Laboratory assessment of platelet functions includes light transmittance aggregation and ATP release assay, glycoprotein assays, electron microscopy, test of procoagulant function, genetic tests (Pai and Hayward, 2009).

The invention therefore relates to a method for diagnosing a platelet disorder comprising the step of using platelets according to the invention in order to standardize platelet function.

Typically, platelets according to the invention can be obtained from megakaryocytic cell lines as described above. They are then used to standardize platelet function in an in vitro diagnostic test. In other words, they are used as a positive control in an vitro diagnostic test for measuring platelet function.

The invention will be further illustrated through the following examples, figures and tables.

Figures

FIG. 1: Quantitation of proplatelet formation at high shear rate, effect of inhibitors and adhesive surfaces. Cells suspended in IMDM were perfused on VWF at $1800\ s^{-1}$ for 10 min, then IMDM alone was perfused for 10 min. Adhesion led to major cell shape changes and to proplatelet formation. Panel A shows the two stages of MK deformations in shear conditions preceding proplatelet and platelet release, compared to undeformed MKs (stage 1); the early deformation characterized by cytoplasm elongation (stage 2); the stage 3 includes later deformation of MKs with cytoskeletal reorganization at a cell pole or both ends, a long thin filament of successive "beads on a thread", the cell then breaks in thin regions. Further exposure to shear generated platelets still associated with long cytoplasmic threads or doublet of platelets as well as round platelets. Quantification is shown on Panel B: (a), MK shape changes were classified into four categories: 1) translocating MKs; 2) early deforming MKs with loss of sphericity; 3) late deforming MKs and elongation of proplatelets; 4) fragmentation of proplatelets and platelet formation. Panel b-f: Distribution of cells in each category relative to the total number of cells counted in 10 fields, as a function of perfusion time. In the absence of inhibitor, modifications of distributions of cord blood MKs (panel b) or bone marrow MKs (panel c) perfused on VWF. Cord blood MKs perfusion on VWF in the presence of GPIb-VWF interaction inhibitors, a blocking antibody to glycocalicin (panel d), or anti-VWF MoAb (panel e), indicated a major inhibition of MK contact on VWF and of subsequent steps, thus abolishing proplatelet formation. Abciximab, blocking the interaction of $\alpha IIb\beta 3$ with VWF, prevented proplatelet and platelet formation (panel f). Representative of 15 experiments. The bar represents 10 μm.

Figure 2:
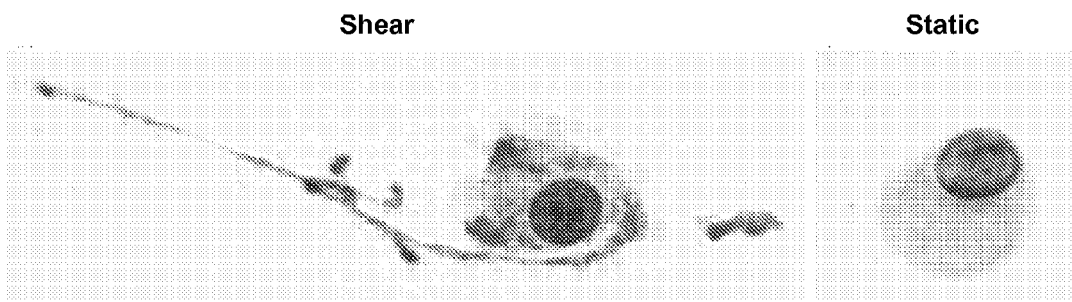

FIG. 2: Light microscopy aspect of cord blood MKs adherent to VWF-coated coverslips under shear or static conditions. Coverslips were removed from the flow chamber and rinsed with PBS prior to fixation in ice-cold methanol and subsequent Romanovsky staining. After exposure to high shear rates for 20 min, numerous MKs displayed long and thin proplatelet extensions oriented parallel to the flow. A single unipolar, long proplatelet extends from the cell core with buddings at its extremity and along the shaft (left panel). As a control of the effect of high shear rate, MKs were deposited on VWF and incubated in static conditions for 20 min, non adherent cells were removed and the coverslip was rinsed with IMDM. Cells displayed a spherical shape, without any proplatelet extension (right panel). Magnification× 500.

Figure 3A:
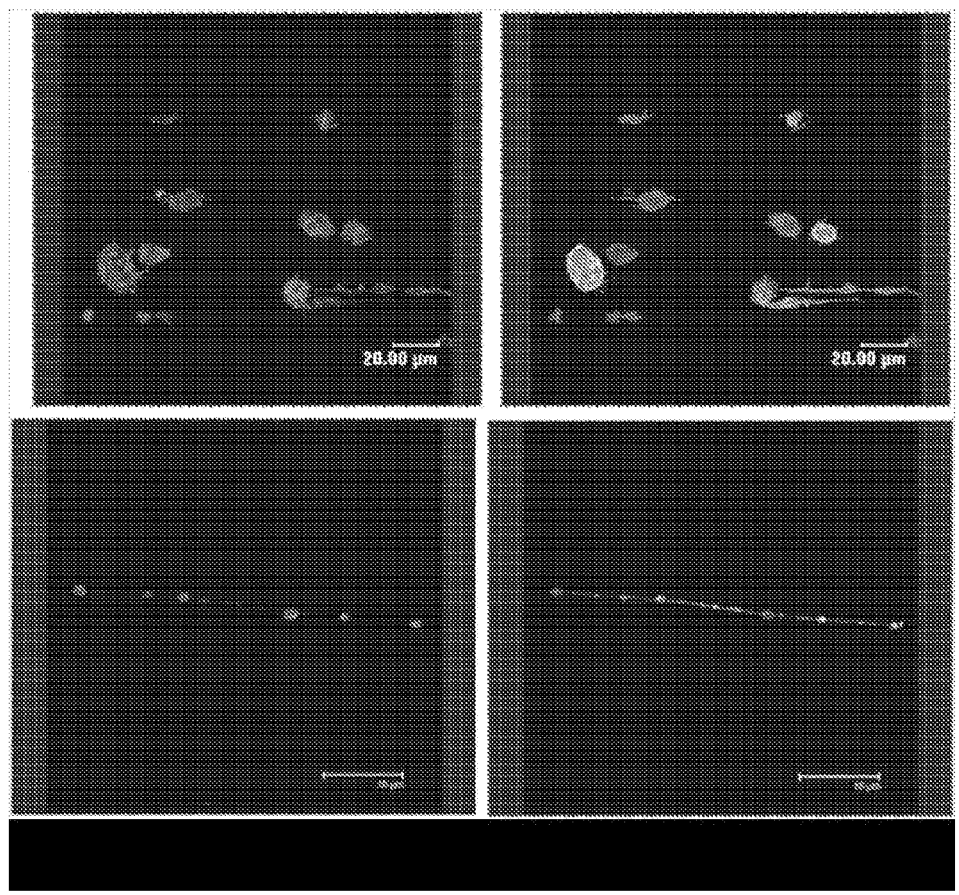

FIG. 3: Role of microtubules in shear-induced proplatelet formation. Panel A: Indirect immunofluorescence labeling with anti-tubulin antibodies showing proplatelet and platelet formation. MKs exposed to a shear rate of 1800 $s^{-1}$ on a VWF-coated surface were fixed and stained with phalloidin (left panels) and anti-tubulin antibodies (right panels). Images were analyzed with a confocal microscope. No colocalisation between actin and tubulin is visible. Panel B: a platelet shedding MK extends a long and thin proplatelet with a platelet-size swollen extremity. The entire proplatelet shaft, as well as its tip, labels for tubulin. Two detached cell fragments display characteristic tubulin labeling: it outlines the dumbbell shaped proplatelet and its central narrowing whereas the platelet-size fragment exhibits a circular labeling pattern. Panel C: effect of microtubule inhibitor on proplatelet. Reversal of proplatelet elongation is characterized by disorganization of tubulin.

Figure 4:
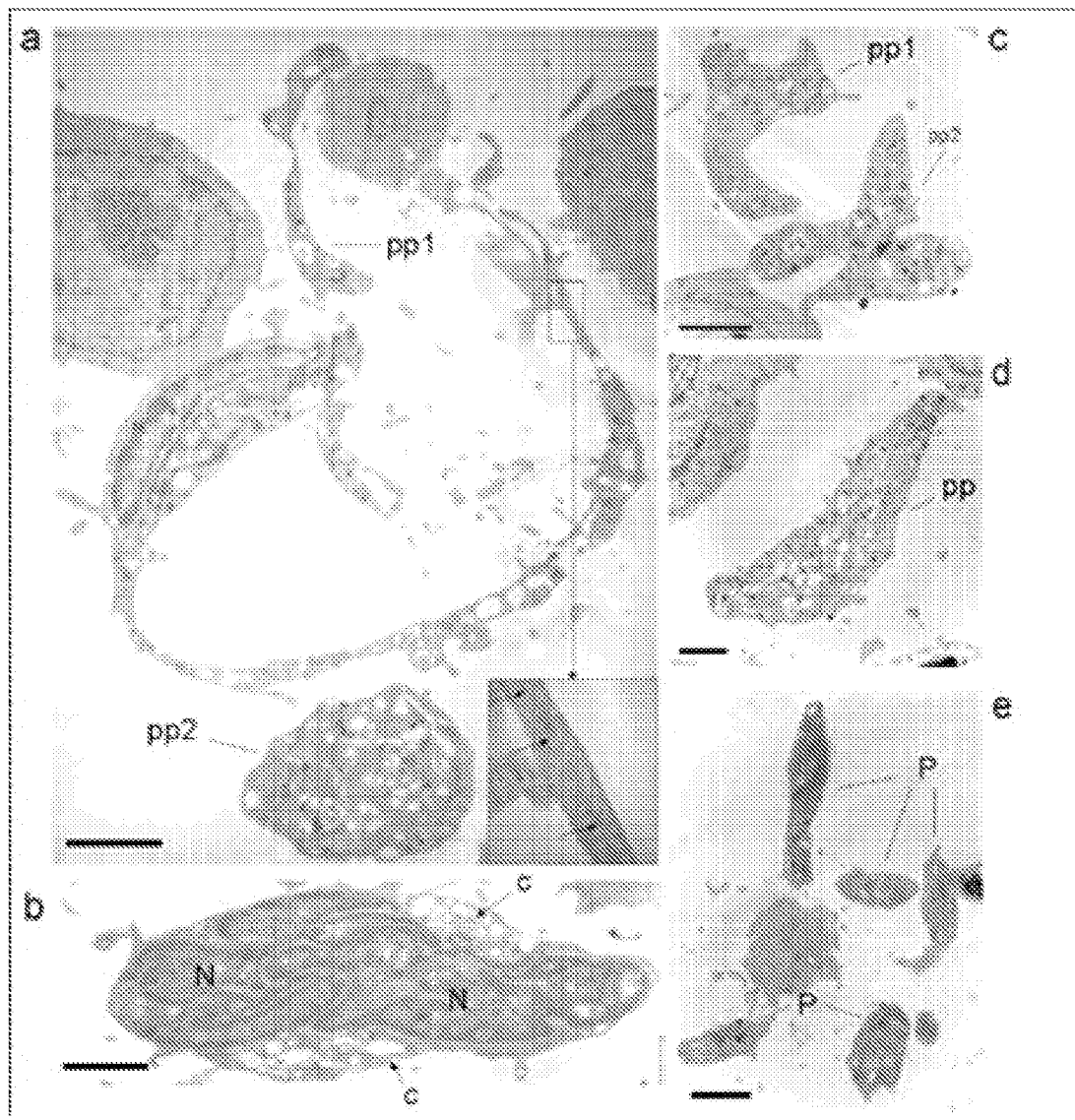

FIG. 4: Ultrastructure of MK exposed to high shear rates leading to platelet formation. Effluent cell suspensions were harvested in fixative directly from the outlet of the perfusion chamber and processed for electron microscopy as described in the Methods section. Mature MKs were elongated, extending long cytoplasmic filopods enclosing parallel longitudinal microtubules (inset). These proplatelets exhibited regular swellings containing cytoplasmic organelles. A large spherical cytoplasmic fragment, probably a detached proplatelet (pp) was located nearby (panel a). The nuclear lobes (N) containing dense chromatin were elongated and located at one pole of the cell. Naked nuclei with an oval shape and compact nuclear lobes containing dense chromatin, which are normally absent form MK cultures, were retrieved in the effluents (panel b). Proplatelets (PP) filled with cytoplasmic organelles appeared as large cytoplasmic fragments, devoid of nuclei, roughly spherical, dumbbell-shaped or elongated with slender extremities (panels c and d). Several isolated platelet-sized fragments (P) were observed (panel e). The bar represents 2 µm.

FIG. 5: Specificity of VWF and high shear rates on proplatelet formation.

Panel A: phase contrast images of proplatelet-froming MK on a VWF-coated coverslip in static conditions (upper panels) and at a high shear rate (lower panels). Proplatelets formed in 14 h and were maximal in 16 h in static conditions, but required only 10 min under flow. Panel B: HUVEC monolayers supported MK adhesion even in the absence of activation (upper panels), while proplatelet formation was seen after HUVEC activation (lower panels). Panel C: MK deformations and proplatelet formation on non-VWF surfaces were minimal in shear conditions as shown for fibrinogen, fibronectin and collagen.

Figure 6:
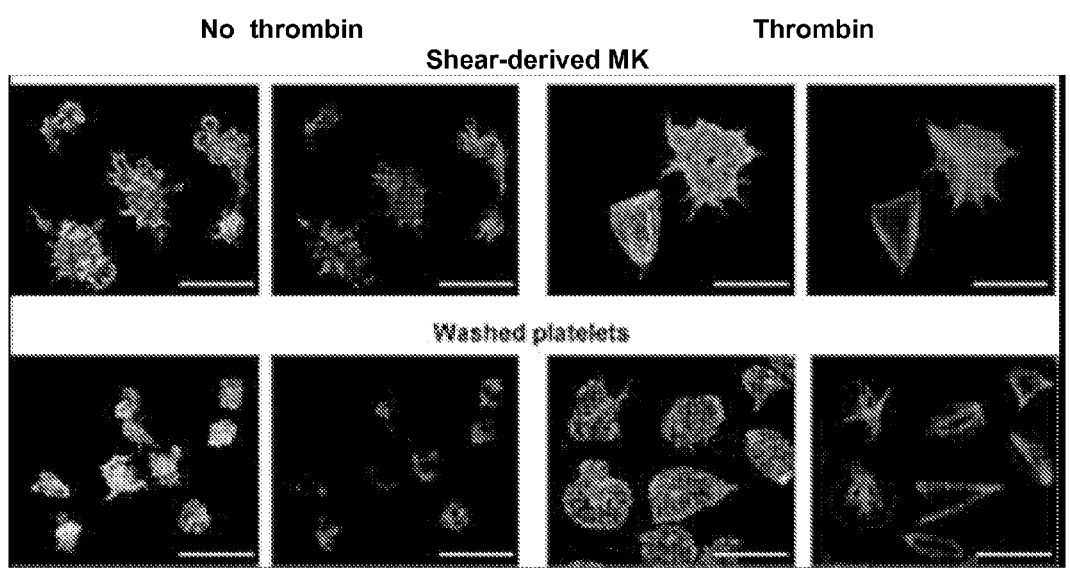

FIG. 6: Platelets obtained from MK exposure to high shear rates can be activated by thrombin. Cell effluents in the flow-through of MKs exposed to high shear rates were analyzed in a fibrinogen adhesion assay in static conditions, followed by confocal microscopy, with cell staining with phalloidin-Alexa 546 to visualize actin and Alexa 488 to visualize $\alpha IIb\beta3$. MK-derived platelets generated by shear exposure (upper panels) adhered to fibrinogen in the absence (left panels) or in the presence of thrombin (right panels). Non-activated cells display diffuse actin staining and $\alpha IIb\beta3$ membrane localization. Following thrombin activation, actin filaments are organized as stress fibers. They display a similar cytoskeletal organization as washed blood platelets prepared in a separate assay without exposure to shear (lower panels). The bar represents 10 µm.

Figure 7:
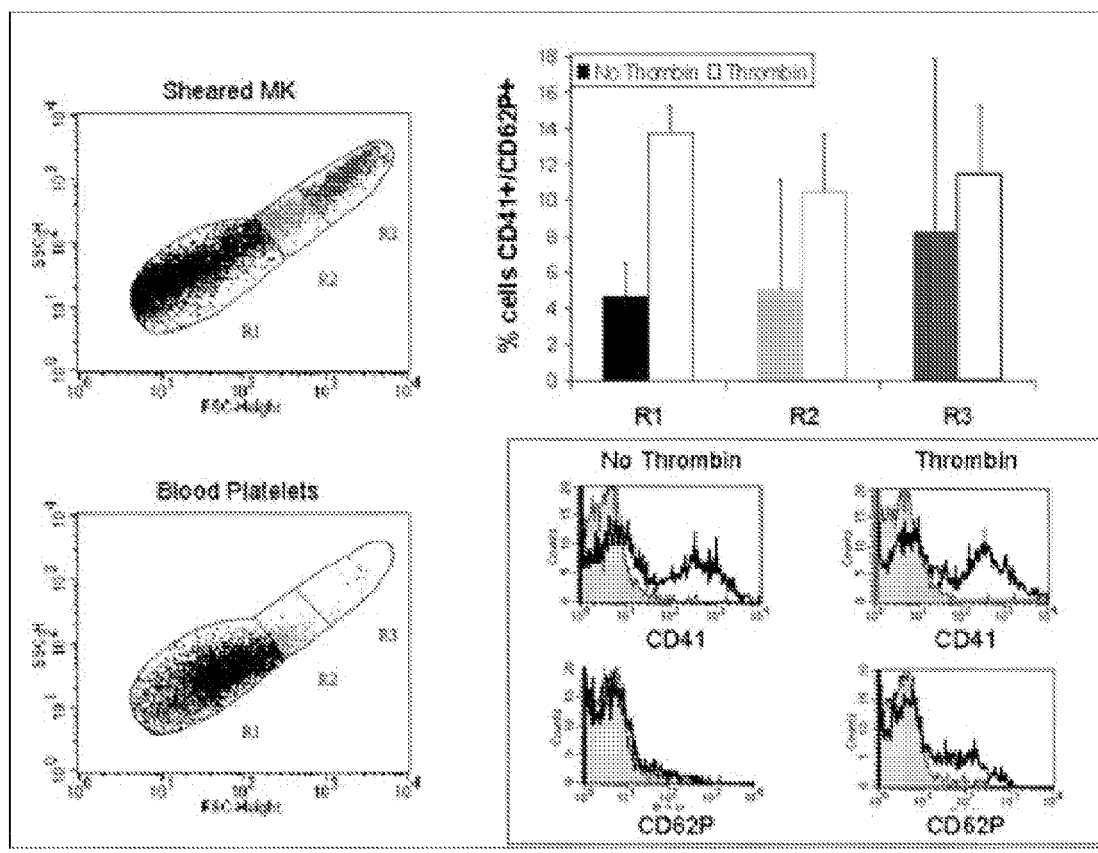

FIG. 7: Released platelets activated by thrombin express P-selectin. Cell effluents were activated or not, by thrombin as described in the legend to FIG. 6, and were analyzed in a flow cytometry assay. Samples were labelled with anti-CD62P-FITC (FL1, P-selectin)) and anti-CD41-PE (FL2, αIIb). Settings of FSC-SSC profiles of washed platelets were used to analyze flow-through cells (top left panel MKs: exposed to shear; bottom left panel: washed platelets). Histogram of CD62P and CD41a double-positive cells, in R1, R2 and R3 regions obtained from dot-plots in the absence (open bars) or presence of thrombin (filled bars). Only thrombin-activated samples contained CD62P-positive cells, while all samples were positive for CD41a (top right panel). Histogram plot of activated platelets (R1) in the flow-through, in the presence of thrombin, following labeling with non-immune IgG (thin line, grey background), anti-CD62P or anti-CD41a (thick line) (bottom right panel).

Figure 8:
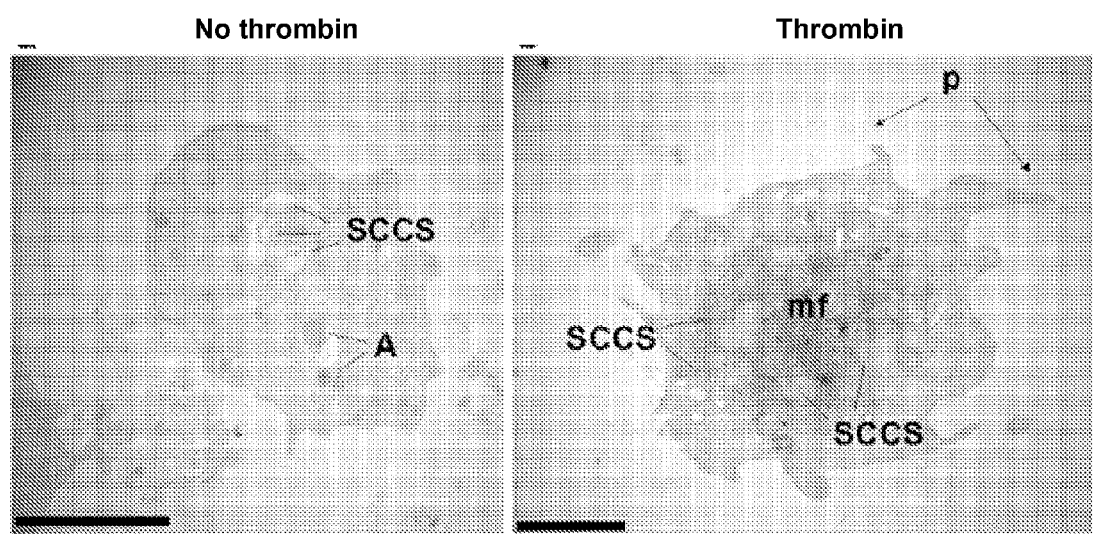

FIG. 8: Ultrastructural modifications of MK-derived platelets following thrombin activation. Cell effluents were activated or not by thrombin, and studied by electron microscopy. In the absence of thrombin, platelet-sized fragments exhibited a smooth surface and contained several alpha granules (A) scattered throughout the cytoplasm, as well as discrete SCCS cisternae (panel a). In the presence of thrombin, the platelet-sized fragments displayed morphological changes characteristic of activated platelets, namely a spherical shape, surface pseudopods (p), dense material within dilated cisternae of SCCS, no granulation in the cytoplasm and a central bundle of microfilaments, reminiscent of activated blood platelets (panel b). The bar represents 2 µm.

EXAMPLE

Material & Methods

Proteins

VWF was a gift of Laboratoire frangais du Fractionnement et des Biotechnologies (Lille, France). Fibrinogen was from Hyphen BioMed (Neuville-sur-Oise, France). Human VWF and fibrinogen were purified and depleted of contaminant fibronectin and of fibrinogen and VWF, respectively (Legendre et al., 2006). Equine tendon collagen was from Nycomed (Munich, Germany) and human fibronectin was from VWR (Fontenay-sous-Bois, France). Wild-type and mutated (V1316M type 2B) recombinant VWF (rVWF) were obtained as described elsewhere (Ajzenberg et al., 2000).

Antibodies

Monoclonal antibody (MoAb) 713, which blocks VWF binding to GPIbα in the presence of ristocetin, was a kind gift of Dr JP Girma (INSERM Unit 770, Le Kremlin-Bicêtre, France) (Ajzenberg et al., 2000). Polyclonal anti-glycocalicin antibody, the extracellular domain of GPIbα containing the VWF binding site, was a kind gift of Dr MC Berndt (Monash University, Melbourne, Australia) (Cramer et al., 1991). Phycoerythrin (PE) conjugated anti-CD62P (P-selectin), fluorescein isothiocyanate (FITC)-conjugated anti-CD41a (αIIb), anti-CD42b (GPIbα) and non-immune antibodies were from Beckman Coulter (Villepinte, France). Anti-α and β-tubulin MoAb were from Amersham (Orsay, France). The anti-β3 integrin P37 MoAb was a gift of Dr Gonzalez-Rodriguez (CSIC, Madrid, Spain) (Calvete et al., 1991). The anti-αIIbβ3 Fab (C7E3) Abciximab (Reopro®) was from Lilly (Suresnes, France).

Human Megakaryocytes

Human MKs used in this study were cultured from precursor cells isolated from umbilical cord blood or bone marrow. Human bone marrow samples (harvested during hip surgery), and cord blood samples were obtained after informed consent in agreement with our Institute Ethic Committee (Assistance Publique des Hôpitaux de Paris) and in accordance with the Declaration of Helsinki. Human umbilical cord blood and bone marrow CD34+ cells were separated by an immunomagnetic technique (StemCell Technologies, Grenoble, France) as previously described (Fichelson et al., 1999). The cells were grown in Iscove's Modified Dulbecco's Medium (IMDM) (Gibco-Invitrogen, Cergy-Pontoise, France) supplemented with 15% BIT 9500 serum substitute (StemCell Technologies) and 20 nmol/L TPO peptide agonist AF13948 (Genosys-Sigma, Saint Quentin Fallavier, France). Ten ng/mL Stem Cell Factor (SCF) (Amgen, Neuilly-sur-Seine, France) were added once, on the first day of culture. MKs cultured for 10 to 16 days in the presence of TPO were fully mature and equipped for platelet biogenesis (Patel et al., 2005a). Cells were showed by flow cytometry to express GPIb and αIIbβ3 (60-70% positive cells). For shear experiments, cells were used between day 10 and 16.

Human Platelets

Blood was obtained from healthy individuals who had not ingested any medication during the previous two weeks. Blood was drawn into 15% (v/v) acid citrate dextrose (ACD) pH 5.8. Washed platelets were prepared from isolated platelet-rich plasma (PRP) in the presence of apyrase (1 U/mL) (Sigma) and ACD (1 mL for 40 mL) (Ajzenberg et al., 2000). Briefly, after washing, platelets were resuspended in Hepes buffer (10 mmol/L Hepes (N-[2-hydroxyethyl]piperazine-N'-[ethanesulfonic acid]), 136 mmol/L NaCl, 2.7 mmol/L KCl and 2 mmol/L MgCl2) pH 7.5 containing 0.15% bovine serum albumin (BSA). Platelets were counted with an electronic particle counter (Model Z1, Coulter Electronics, Margency, France), and concentration adjusted to $1.5 \times 10^8$ platelets/mL.

Mouse Megakaryocytes and Platelets

Wild-type C57BL/6J mice were used at 7-10 weeks of age. Animal care and procedures were in accordance with institutional guidelines. Megakaryocytes were expanded and separated from flushed bone marrows. Briefly, immunomagnetically purified Lin—cells were grown in appropriate megakaryocyte differentiation medium in the presence of TPO-peptide. After 6 days in culture, mature megakaryocytes were introduced in a miniaturized flow chamber (Conant et al., 2009) and perfused on immobilized mouse recombinant VWF (Marx et al., 2008) at high shear rates.

Perfusion Studies

Perfusion studies were performed using a previously published flow chamber obtained from Maastricht Instrumentation (Legendre et al., 2006). The flow chamber consisted of a rectangular cavity 0.05 mm high, 29 mm long, and 5 mm wide, carved in a Plexiglas block. The bottom of the chamber was lined with a glass coverslip coated overnight at 4° C. with VWF (20 µg/mL) diluted in Tris-buffered saline (TBS, 25 mmol/L Tris-HCl, pH 7.4, 150 mmol/L NaCl). In some experiments, another purified protein (fibronectin, fibrinogen, collagen or type 2B-rVWF was tested. MKs in suspension in IMDM (2 mL) at a concentration of $0.8-1 \times 10^6$ cells/mL were drawn in a 5-mL glass gas-tight microsyringe (Exmine, Ito Corporation, Fuji, Japan) connected to the chamber with an extension set (Steritex, Codan, Lensahn, Germany). A flow rate of 225 µL/min was applied with an electric pump, generating a shear rate of 1800 s−1. The cells were perfused for 10 min, followed by IMDM perfusion at the same shear rate for 10 min. All experiments were performed at 37° C. maintained with a Minitüb heating system (Minitüb Abfüll and Labortechnik, Tiefenbach, Germany). In some experiments, cells or coverslips were preincubated with antibodies for 10 min prior to perfusion. After the end of the perfusion, the coverslip was fixed with ice-cold methanol for 5 min, washed with distilled water, dried, and stained. Effluents were collected at the exit of the chamber for further studies, including thrombin activation.

Videomicroscopy System

The perfusion chamber was placed on the stage of an inverted microscope (Axiovert 135, Zeiss, Germany). A CCD camera (Sony, Tokyo, Japan) was used to visualize cells, using a 20× Hoffman modulation contrast objective. Continuous recording was performed with a digital image recorder (Replay Software, Microvision Instruments, Evry, France) connected to a video timer (VTG, Tokyo, Japan). Image frames were analysed with Histolab or Videomet quantification software (Microvision Instruments).

Cell Activation Studies and Flow Cytometry.

Effluent cell suspensions were collected and centrifuged in the presence of 0.5 mmol/L EDTA at 1800 rpm for 12 min, and the pellets were resuspended in IMDM. Aliquots were incubated in the absence or presence of thrombin (0.5 U/mL) for 10 min at 37° C. Cells in suspension (100 µL) were incubated for 20 min at room temperature with FITC-anti-CD62P and PE-anti-CD41a (5 µL of each) or non immune conjugated control antibody, before adding 300 µL PBS. The cells were then analyzed with a FACSort flow cytometer (Becton-Dickinson, Le Pont-de-Claix, France); 10 000 events were acquired with settings on the platelet region identified by their characteristic profile on a right-angle scatter (SSC) and forward-angle scatter (FSC) plot determined in separate experiments with unstimulated washed platelets.

Confocal Immunofluorescence

Aliquots (150 µL) of unactivated and thrombin-activated cells were added to fibrinogen-coated glass Lab-Tek chamber slides (Nunc, Rochester, N.Y.) incubated for 30 min in static conditions. Non adherent cells were removed and the slides were washed three times with PBS, before fixation with 2% paraformaldehyde (Carlo Erba, Val de Reuil, France) in PBS for 30 minutes and storage at 4° C. For immunofluorescent staining, the cells were permeabilized for 5 min with 0.1% Triton X-100 in PBS, then incubated for 30 min with the anti-β3 P37 MoAb (10 µg/mL in PBS), washed and incubated with 20 µg/mL of the secondary antibody conjugated to AlexaFluor 488 (Molecular Probes, Eugene, Oreg.). The negative control used purified IgG from mouse ascites at the same protein concentration. For actin labeling, permeabilized cells were incubated at room temperature for 30 min with 50 µL of 30 nmol/L AlexaFluor 546 phalloidin (Molecular Probes) in PBS containing 3% BSA. The coverslips were then washed twice and mounted in mounting solution containing TOTO3 and Vectashield (Vector Laboratories, Peterborough, UK). AlexaFluor488/AlexaFluor546 staining was analysed with a Leica TCS SP2 AOBS confocal microscope.

Electron Microscopy

Effluent cell suspensions were harvested in glutaraldehyde fixative (1.5% final concentration in phosphate buffer 0.1M, pH 7.4) directly at the exit from the perfusion chamber, after passage over various matrices and were then processed for electron microscopy as previously described (Cramer et al., 1997). Some samples were first activated by thrombin as above and further treated for electron microscopy. Examination was performed on a Jeol 10-11 electron microscope (Jeol Ltd, Tokyo, Japan).

Statistics

We used Student's unpaired t-test for statistical analysis; P values<0.05 were considered significant. Error bars represent the standard error of the mean (SEM).

Results

Dynamic Interactions of MKs with VWF

Cord blood mature MKs were perfused at varying shear rates on a surface coated with purified VWF. At 1800 $s^{-1}$, MKs established transient interactions with VWF, slowing down the velocity of MKs rolling on VWF and progressively leading to profound morphological changes that finally led to platelet shedding from MKs. The different steps of platelet formation are summarized in FIG. 1A. The process starts with roughly spherical MKs, then the cell periphery deforms and pseudopods become visible on adherent MKs (stage 2). Elongation of the cytoplasm then takes place, organized along the flow, at the rear and/or the front of the cell body (Stage 3). Intermediate swellings with a characteristic beads-on-a-thread aspect start to appear. Elongation occurred rapidly, at a velocity of 21 μm/min, thus 25-fold higher than reported in static conditions (Patel et al., 2005b). Interestingly, fragmentation occurred not only at the tip of these extensions, but also between the swellings, in particular in thinner constrictions, releasing fragments of varying sizes, and most often several beads still attached together, but devoid of the main cell body (FIG. 1A). Finally, these fragments were further broken down into smaller particles, the size of a platelet, clearly visible during late time points (FIG. 1A). Proplatelet fragmentation occurred rapidly within 15-20 min under high shear rate conditions. Similar results were obtained by using cord blood derived MKs or bone marrow derived MKs. In contrast, in the absence of flow or at lower shear rates (<1000 $s^{-1}$), no proplatelet and platelet release was seen during the 20 min period of MK contact with VWF. Shear exposure of immature MKs, cultured less than 9 days, did not allow translocation and fragmentation.

Specificity of VWF Interaction with MK Receptors in Platelet Formation

Figure 1B:
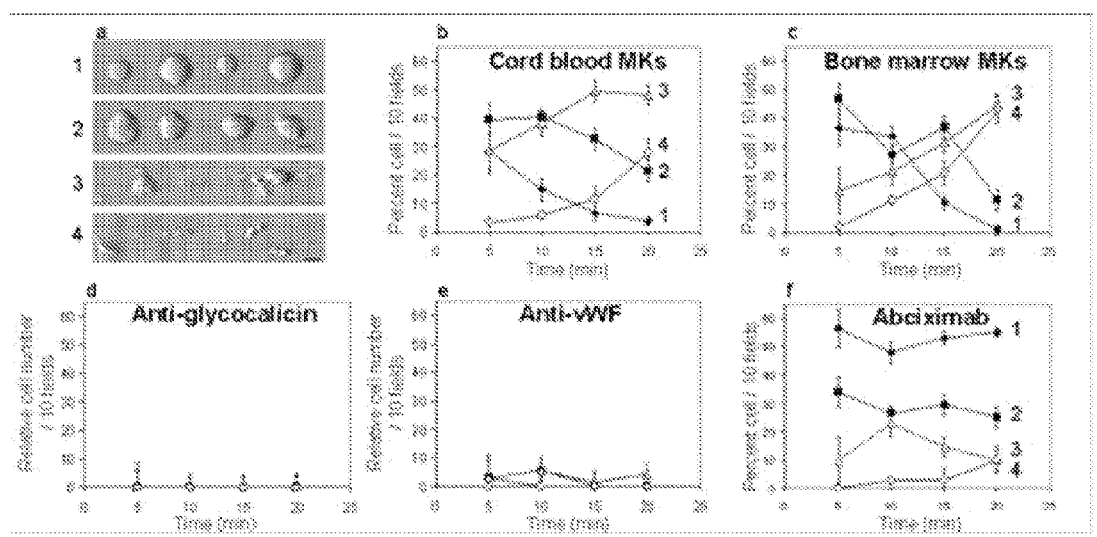

Four cell categories were defined in order to quantify morphological changes during shear exposure: 1) translocating MKs; 2) early deforming MKs with loss of sphericity; 3) late deforming MKs with proplatelet elongation; and 4) proplatelet fragmentation and platelet release (FIG. 1B, panel a). There was a gradual increase in the proportion of elongated cells and proplatelets and platelets, reaching 27.6±4.9% of cells at 20 min. This increase mirrored the decrease in translocating cells from 28.2±6.5 at 5 min to 3.6±1.6% at 20 min, and the decrease in early deforming MKs (FIG. 1B, panel b). Results similar to those described with cord blood MKs were obtained when measuring the distribution of bone marrow MKs exposed to high shear rate (FIG. 1B, panel c). MK translocation and subsequent steps including proplatelet formation and platelet release were completely abolished in the presence of an antibody directed against glycocalicin or the GPIb-binding domain of VWF (FIG. 1B, panels d and e), demonstrating the crucial importance of the VWF-GPIb interaction. In the presence of the αIIbβ3 inhibitor Abciximab, the proportion of cells without proplatelet (undeforming and early deforming MKs) remained constant in time, whereas proplatelet elongation was strongly reduced and platelet formation was almost completely abolished (FIG. 1B, panel f). This inefficient proplatelet formation was due to loose contact with the VWF surface (data not shown).

Figure 3B:
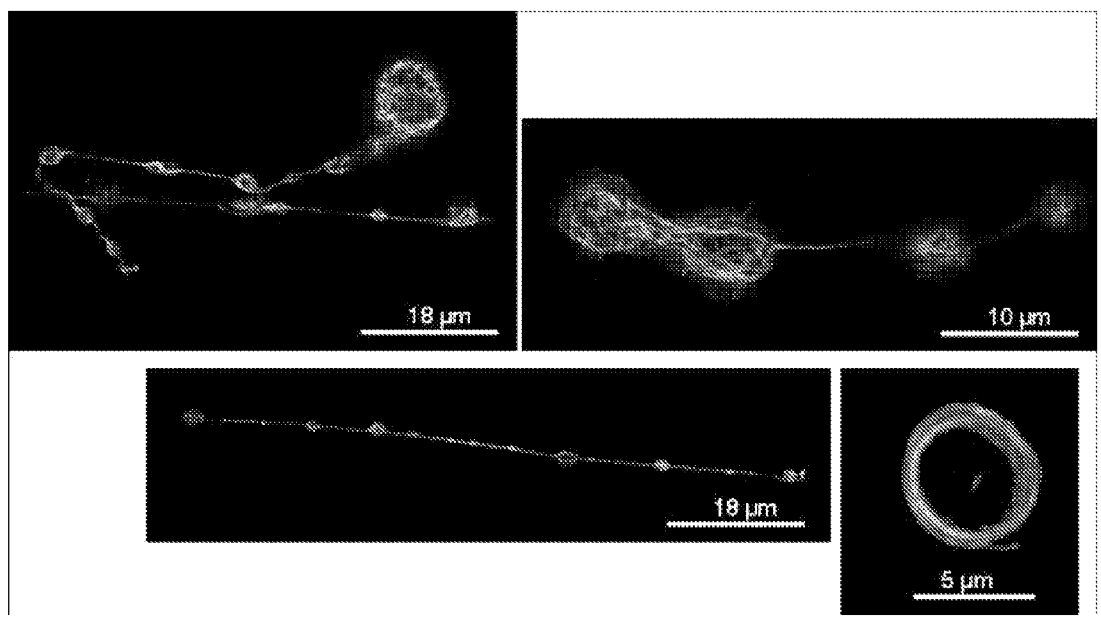
Figure 3C:
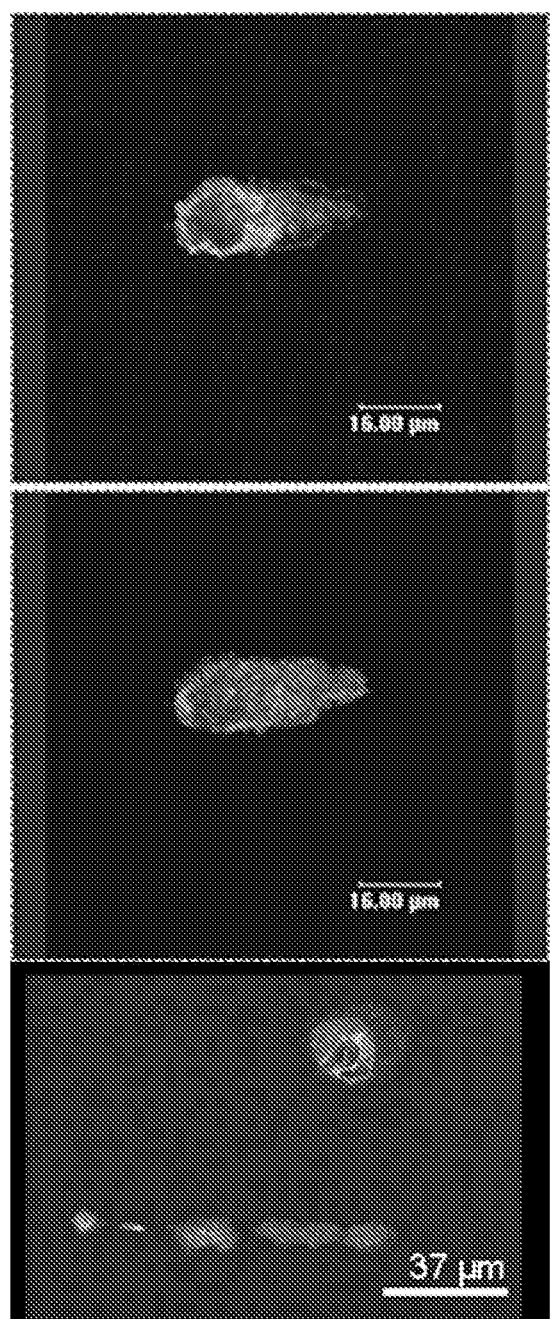

Characterization of Platelet Formation Induced by MK Exposure to a High Shear Rate Shear forces applied to mature MKs induced specific morphological changes as compared to a control performed by incubating the cells in static conditions for 20 min on VWF, where the morphology of MKs remained unchanged with respect to that of the cells before contact with VWF (FIG. 2). In contrast, post-fixation staining of VWF-coated coverslips after 20 min of MK perfusion showed that MKs extended long filopods at their tip and that beaded platelet-like spikes were formed along the shaft, as well as larger cytoplasmic fragments (FIG. 2). Proplatelet elongation requires the sliding of overlapping microtubules staining for α and β1 tubulin (Patel et al., 2005b). We found that MK extensions were stained by anti tubulin antibody in different territories than actin, confirming that these extensions displayed similar staining as identified in proplatelet forming MKs by the work of Italiano et al. (Italiano et al., 2003; Italiano et al., 1999; Patel et al., 2005a; Patel et al., 2005b); tubulin labeling followed the proplatelet shaft in elongated MKs and displayed a ring pattern on spherical MKs, on proplatelets and on platelets (FIG. 3B). The importance of microtubules in shear-induced proplatelet formation, was confirmed by preincubation with Nocodazole, an inhibitor of microtubule assembly, that completely prevented MK elongation and proplatelet formation in flow conditions (data not shown). To demonstrate that Nocodazole was not acting on preformed platelets in cell suspensions, the microtubule inhibitor was added after elongation; the effect visualized in real-time showed that Nocodazole could revert the shear-induced elongation when added after the process had occurred. The specificity of reversal was confirmed by tubulin staining. Interestingly, following Nocodazole addition at 25 min, tubulin was no longer organized was seen in proplatelets and platelets, thus indicating that the elongated processes were different from tethers (FIG. 3C). Indeed, membrane tethers are dynamic structures extending from small, localized adhesion contacts under the influence of flow, are induced by VWF-GP Ib interaction, but they do not display any tubulin staining (Dopheide et al., 2002).

Electron microscopy showed long cytoplasmic shafts extending from the cell core, containing parallel bundles of microtubules and were sometimes swollen with cytoplasmic organelles (FIG. 4, panel a). Nuclear lobes with dense heterochromatin were located at one pole of the cell and naked nuclei were occasionally seen (FIG. 4, panel b). Large cytoplasmic fragments, devoid of nuclei, were roughly spherical, dumbbell-shaped or elongated with slender extremities (FIG. 4, panels c and d). Platelet-like fragments were also visible (FIG. 4, panel e).

Proplatelet Formation is Accelerated by High Shear Rate and VWF

Figure 5A:
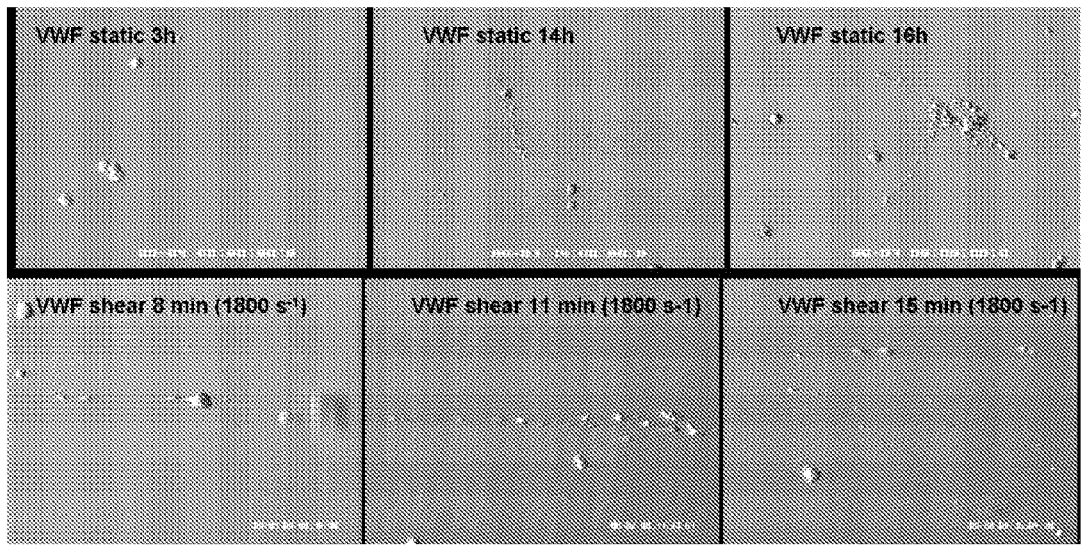
Figure 5B:
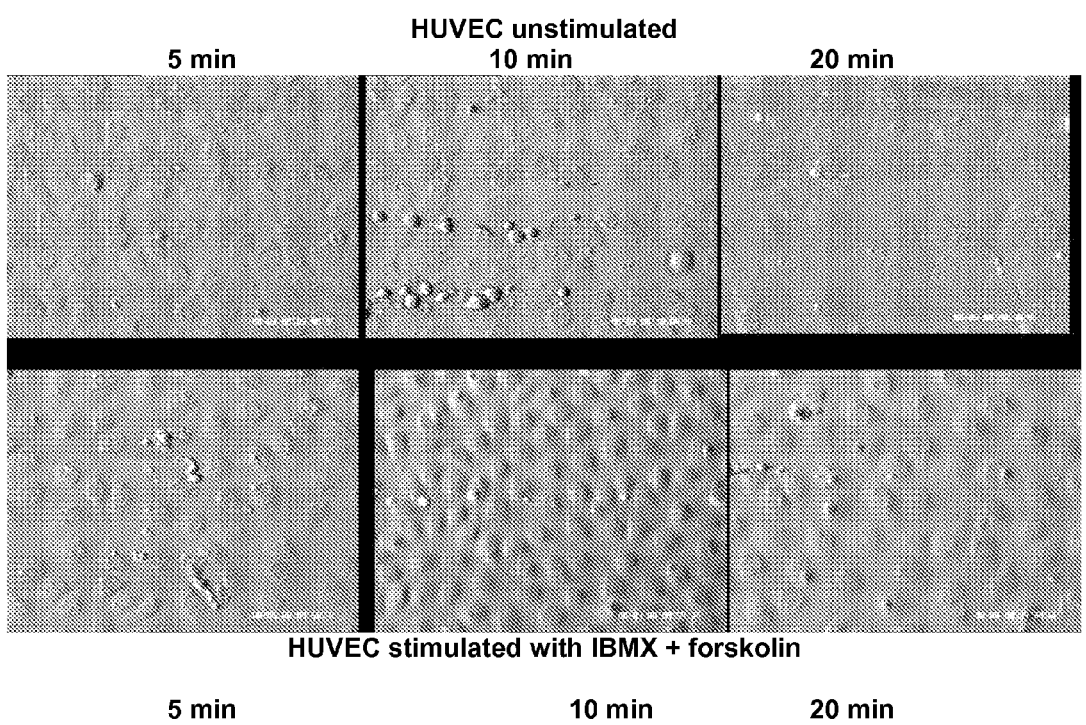
Figure 5C:
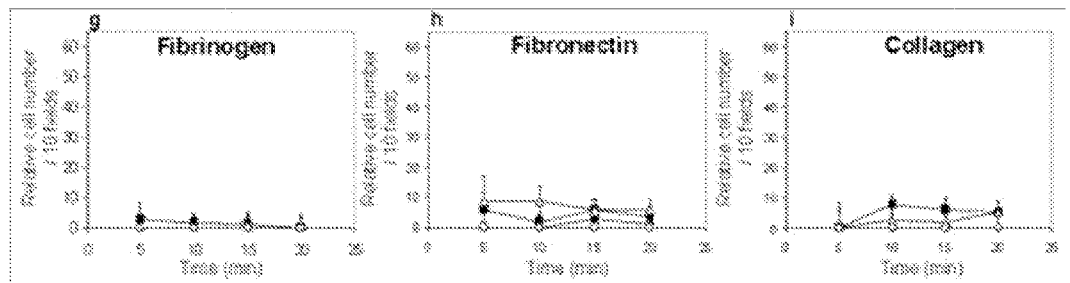

It has been recently demonstrated that adhesive proteins are involved in the regulation of proplatelet formation; in particular, proplatelet formation occurred in 16 hours after MK plating on VWF in static conditions (Balduini et al., 2008). As shown in FIG. 5A, we obtained similar findings. In contrast, in the presence of high shear rate, the process occurred very rapidly, since within 20 min, 70% from cord blood MKs and 80% from bone marrow MKs, formed proplatelets. This effect was dependent on the extent of shear rate (600-2400 $s^{-1}$) and on cell concentration (0.5-2×10$^6$/mL). Endothelial cells contain high molecular weight multimers of VWF that are released constitutively at a low rate and are increased in inflammatory conditions (Rondaij et al., 2006). We therefore assessed whether VWF released from an endothelial cell matrix would support MK adhesion and proplatelet formation. MKs rolled and adhered on unstimulated HUVEC, but proplatelet formation occurred on stimulated HUVECs (FIG. 5B). Platelet formation occurs also on an endothelial cell matrix that underlies the endothelial cell layer, and is present once these endothelial cells are removed. In addition, we studied proplatelet formation from MKs perfused on a surface coated with a mutated type 2B rVWF. We selected the V1316M substitution, a well-defined mutation, characterized by enhanced VWF binding to platelet GPIb with mild thrombocytopenia and giant platelets (Ajzenberg et al., 2000; Miura et al., 2000). We found that the mean velocity of MK translocation on type 2B-rVWF (4.6±0.3 µm/s) was much lower than on wild type (wt)-rVWF (33.6±2.5 µm/s, p<0.0001). All steps of proplatelet formation by MKs exposed to high shear rates were slower on 2B-rVWF than wt-rVWF, leading to decreased platelet production and increased proplatelet accumulation (data not shown). Finally, to further establish the specificity of adhesive surface in the regulation of proplatelet formation, we examined the extent of proplatelet formation by MKs perfused over fibrinogen, collagen or fibronectin at a high shear rate. No proplatelet was formed on these surfaces; the only change was a mild early MK deformation on fibrinogen (FIG. 5C).

Platelets Generated by MK Shear Exposure are Functional

Platelet adhesion to fibrinogen mediated by αIIbβ3 integrin occurs in the absence of activation and is reinforced upon thrombin activation of this receptor. To confirm that platelets generated by MK shear exposure were structurally and functionally similar to blood platelets, cells collected in the flow-through were compared to isolated blood platelets, in a static adhesion assay to fibrinogen (Mazharian et al., 2007). Cells were firmly adherent to fibrinogen in the absence of thrombin, demonstrating that αIIbβ3 was functional in shear-induced platelets and proplatelets. Non-activated elements displayed diffuse actin staining and αIIbβ3 membrane localization. Following thrombin activation, actin filaments were reorganized both in nucleated and anucleated elements, showing lamellipod and filopod formation, and integrin membrane staining (FIG. 6). These MK-derived platelets generated by shear exposure displayed a similar cytoskeletal organization as washed blood platelets prepared in a separate assay without exposure to shear (FIG. 6).

Flow cytometry analysis of shear-exposed cells showed three populations of CD41 positive cells, according to their size. The smaller sized population overlapped with that of blood platelets, while the intermediate one corresponded to larger elements, including proplatelets and naked nuclei (FIG. 7). Thus, the platelet population produced by exposure to shear includes a higher proportion of intermediate sized platelets, compared to platelets isolated from peripheral blood. Sheared MKs belonged to the same large size population as unsheared MKs. In response to thrombin stimulation, upregulation of P-selectin (CD62P) was seen on the surface of shear-derived platelets (11.8±1.8% compared to 6.2±0.9% for non activated platelets, p=0.0005). Similarity with isolated blood platelets was confirmed by ultrastructural data (FIG. 8). In the absence of thrombin, the platelet-like fragments exhibited a smooth surface, several alpha granules scattered in the cytoplasm and discrete surface connected canalicular system (SCCS) (FIG. 8). Following thrombin activation, these cells displayed morphological changes typical of activated platelets, namely a spherical shape, surface pseudopods, dense material within centralized and dilated cisternae of SCCS, no cytoplasmic granulation and a central bundle of microfilaments (FIG. 8). Finally, to confirm that platelet-sized elements were generated by shear exposure and did not simply arise in suspension of mature MK, the effluents were compared before and after perfusion in the flow chamber, by the presence of naked nuclei. Non adherent flow through of cells exposed to shear contained more naked nuclei than cells in static conditions that were devoid of them (data not shown).

Mouse Megakaryocytes and Platelets

Exposure of mouse mature megakaryocytes to high shear rates on mouse VWF resulted in efficient platelet formation. In a series of experiments, extraction of bone marrow derived cells from 6-8 animals allowed the production of at least 6-12×10$^6$ mature megakaryocytes. These cells were exposed to a shear rate of 1800 $s^{-1}$ during 90 minutes and were completely converted into small elements corresponding to the platelet size. Characterization of mouse platelets by confocal immunofluorescence revealed the specific tubulin ring in platelet-size elements. The aggregation properties in response to agonists of these platelets is established by standard techniques in an aggregometer.

Injection of Platelets According to the Invention to Thrombocytopenic Mice Rescues the Bleeding Phenotype This experiment aims at rescuing the bleeding phenotype of a thrombocytopenic recipient mouse, by infusion of donor mouse platelets generated by high shear forces, as described above.

Recipient mice are injected via the tail vein with the platelets obtained by shear exposure of bone marrow mature megakaryocytes obtained from pooled donor mice. Thrombocytopenic mice are obtained by administration of low concentrations of an antibody against GPIIb-IIIa (Nieswandt et al., 2000). In a typical experiment, we obtain an 80% reduction of circulating platelets by 2-3 injections of an anti-GPIIb antibody. These platelets are fluorescently labeled prior to injection to the thrombocytopenic mouse for detection and clearance studies. Correction of platelet counts, spontaneous bleeding and bleeding time in infused mice is determined. These circulating fragments are active platelets as they increase platelet numbers and correct the blood loss in in vivo models of induced bleeding. We use a model of irritant contact dermatitis that results in massive hemorrhage limited to the area of inflammation (Goerge et al., 2008). Skin bleeding in thrombocytopenic mice is compared before and after administration of shear-generated platelets. The function of newly formed platelets is also assessed in vivo with the thrombosis model of ferric chloride injury by intravital microscopy (Denis et al., 1998). This method provides detailed information on the different steps of the thrombotic process, that include single-platelet adhesion, rate of thrombus growth, thrombus stability, emboli size and time to occlude the vessel (Denis and Wagner, 2007). We compare real-time thrombus formation and incorporation of platelets in the thrombus before and after administration of platelets in thrombocytopenic mice.

CONCLUSION

In conclusion, the finding that mature MK interaction with VWF in flow conditions promotes human/mouse proplatelet formation represents a major breakthrough in understanding platelet formation, which may thus occur in capillaries or small arteries. The exploration of diseases with decreased platelet production would greatly benefit of a better understanding of platelet shedding from megakaryocytes. Finally, the inventors' results provide a method for platelet production for diagnostic or therapeutic purposes.

REFERENCES

Ajzenberg, N., A. S. Ribba, G. Rastegar-Lari, D. Meyer, and D. Baruch. 2000. Effect of recombinant von Willebrand factor reproducing type 2B or type 2M mutations on shear-induced platelet aggregation. *Blood.* 95:3796-803.

Balduini, A., I. Pallotta, A. Malara, P. Lova, A. Pecci, G. Viarengo, C. L. Balduini, and M. Torti. 2008. Adhesive receptors, extracellular proteins and myosin IIA orchestrate proplatelet formation by human megakaryocytes. *J Thromb Haemost.* 6:1900-1907.

Barroga, C. F., H. Pham, and K. Kaushansky. 2008. Thrombopoietin regulates c-Myb expression by modulating micro RNA 150 expression. *Experimental Hematology.* 36:1585-1592.

Calvete, J. J., A. Henschen, and J. Gonzalez-Rodriguez. 1991. Assignment of disulphide bonds in human platelet GPIIIa. A disulphide pattern for the beta-subunits of the integrin family. *Biochem J.* 274 (Pt 1):63-71.

Conant, C. G., M. A. Schwartz, T. Nevill, and C. Ionescu-Zanetti. 2009. Platelet adhesion and aggregation under flow using microfluidic flow cells. *J Vis Exp.* 32:1644 [pii].

Cramer, E. M., H. Lu, J. P. Caen, C. Soria, M. C. Berndt, and D. Tenza. 1991. Differential redistribution of platelet glycoproteins Ib and IIb-IIIa after plasmin stimulation *Blood.* 77:694-699.

Cramer, E. M., F. Norol, J. Guichard, J. Breton-Gorius, W. Vainchenker, J. -M. Masse, and N. Debili. 1997. Ultrastructure of Platelet Formation by Human Megakaryocytes Cultured With the Mpl Ligand. *Blood.* 89:2336-2346.

Debili, N., N. Kieffer, M. Nakazawa, J. Guichard, M. Titeux, E. Cramer, J. Breton-Gorius, and W. Vainchenker. 1990. Expression of platelet glycoprotein Ib by cultured human megakaryocytes: ultrastructural localization and biosynthesis. *Blood.* 76:368-376.

Denis, C., N. Methia, P. S. Frenette, H. Rayburn, M. Ullman-Cullere, R. O. Hynes, and D. D. Wagner. 1998. A mouse model of severe von Willebrand disease: Defects in hemostasis and thrombosis. *Proc Natl Acad Sci USA.* 95:9524-9529.

Denis, C. V., and D. D. Wagner. 2007. Platelet Adhesion Receptors and Their Ligands in Mouse Models of Thrombosis. *Arterioscler Thromb Vasc Biol.* 27:728-739.

Dopheide, S. M., M. J. Maxwell, and S. P. Jackson. 2002. Shear-dependent tether formation during platelet translocation on von Willebrand factor. *Blood.* 99:159-167.

Dunois-Larde, C., C. Capron, S. Fichelson, T. Bauer, E. Cramer-Borde, and D. Baruch. 2009. Exposure of human megakaryocytes to high shear rates accelerates platelet production. *Blood.* 114:1875-1883.

Federici, A. B. 2005. Management of von Willebrand disease with factor VIII/von Willebrand factor concentrates: results from current studies and surveys. *Blood Coagul Fibrinolysis.* 16 Suppl 1:S17-21.

Fichelson, S., J. -M. Freyssinier, F. Picard, M. Fontenay-Roupie, M. Guesnu, M. Cherai, S. Gisselbrecht, and F. Porteu. 1999. Megakaryocyte Growth and Development Factor-Induced Proliferation and Differentiation Are Regulated by the Mitogen-Activated Protein Kinase Pathway in Primitive Cord Blood Hematopoietic Progenitors. *Blood.* 94:1601-1613.

Fujimura, Y., K. Titani, L. Z. Holland, S. R. Russell, J. R. Roberts, J. H. Elder, Z. M. Ruggeri, and T. S. Zimmerman. 1986. von Willebrand factor. A reduced and alkylated 52/48-kDa fragment beginning at amino acid residue 449 contains the domain interacting with platelet glycoprotein 1b. *J. Biol. Chem.* 261:381-385.

Girma, J. P., M. W. Chopek, K. Titani, and E. W. Davie. 1986a. Limited proteolysis of human von Willebrand factor by Staphylococcus aureus V-8 protease: isolation and partial characterization of a platelet-binding domain. *Biochemistry.* 25:3156-63.

Girma, J. P., M. Kalafatis, G. Pietu, J. M. Lavergne, M. W. Chopek, T. S. Edgington, and D. Meyer. 1986b. Mapping of distinct von Willebrand factor domains interacting with platelet GPIb and GPIIb/IIIa and with collagen using monoclonal antibodies. *Blood.* 67:1356-66.

Goerge, T., B. Ho-Tin-Noe, C. Carbo, C. Benarafa, E. Remold-O'Donnell, B. -Q. Zhao, S. M. Cifuni, and D. D. Wagner. 2008. Inflammation induces hemorrhage in thrombocytopenia. *Blood.* 111:4958-4964.

Goudemand, J., I. Scharrer, E. Berntorp, C. A. Lee, A. Borel-Derlon, N. Stieltjes, C. Caron, J. M. Scherrmann, F. Bridey, Z. Tellier, A. B. Federici, and P. M. Mannucci. 2005. Pharmacokinetic studies on Wilfactin, a von Willebrand factor concentrate with a low factor VIII content treated with three virus-inactivation/removal methods. *J Thromb Haemost.* 3:2219-2227.

Greenberg, S. M., D. S. Rosenthal, T. A. Greeley, R. Tantravahi, and R. I. Handin. 1988. Characterization of a new megakaryocytic cell line: the Dami cell. *Blood.* 72:1968-1977.

Houdijk, W. P., M. E. Schiphorst, and J. J. Sixma. 1986. Identification of functional domains on von Willebrand factor by binding of tryptic fragments to collagen and to platelets in the presence of ristocetin. *Blood.* 67:1498-1503.

Huizinga, E. G., S. Tsuji, R. A. Romijn, M. E. Schiphorst, P. G. de Groot, J. J. Sixma, and P. Gros. 2002. Structures of glycoprotein Ibalpha and its complex with von Willebrand factor A1 domain. *Science.* 297:1176-9.

Isakari, Y., S. Sogo, T. Ishida, T. Kawakami, T. Ono, T. Taki, and H. Kiwada. 2009. Gene Expression Analysis during Platelet-Like Particle Production in Phorbol Myristate Acetate-Treated MEG-01 Cells. *Biological & Pharmaceutical Bulletin.* 32:354-358.

Italiano, J. E., Jr., W. Bergmeier, S. Tiwari, H. Falet, J. H. Hartwig, K. M. Hoffmeister, P. Andre, D. D. Wagner, and R. A. Shivdasani. 2003. Mechanisms and implications of platelet discoid shape. *Blood.* 101:4789-4796.

Italiano, J. E., Jr., P. Lecine, R. A. Shivdasani, and J. H. Hartwig. 1999. Blood Platelets Are Assembled Principally at the Ends of Proplatelet Processes Produced by Differentiated Megakaryocytes. *J Cell Biol.* 147:1299-1312.

Kauskot, A., F. Adam, A. Mazharian, N. Ajzenberg, E. Berrou, A. Bonnefoy, J. -P. Rosa, M. F. Hoylaerts, and M. Bryckaert. 2007. Involvement of the Mitogen-activated Protein Kinase c-Jun NH2-terminal Kinase 1 in Thrombus Formation. *J Biol Chem.* 282:31990-31999.

Legendre, P., A. Salsmann, J. Rayes, O. Trassard, N. Kieffer, and D. Baruch. 2006. CHO cells expressing the high affinity alphaIIbbeta3T562N integrin demonstrate enhanced adhesion under shear. *J Thromb Haemost.* 4:236-246.

Marx, I., O. D. Christophe, P. J. Lenting, A. Rupin, M. -O. Vallez, T. J. Verbeuren, and C. V. Denis. 2008. Altered thrombus formation in von Willebrand factor-deficient mice expressing von Willebrand factor variants with defective binding to collagen or GPIIbIIIa. *Blood.* 112:603-609.

Mazharian, A., S. Roger, E. Berrou, F. Adam, A. Kauskot, P. Nurden, M. Jandrot-Perrus, and M. Bryckaert. 2007. Protease-activating Receptor-4 Induces Full Platelet Spreading on a Fibrinogen Matrix: involvement of ERK2 and p38 and Ca2+ mobilization. *J. Biol. Chem.* 282:5478-5487.

Mekrache, M., N. Kieffer, and D. Baruch. 2002. Activation of recombinant [alpha]IIb[beta]3 expressed in Chinese hamster ovary cells exposes different binding sites for fibrinogen or von Willebrand factor: evidence using monoclonal antibodies to [alpha]IIb[beta]3. *Br J Haematol.* 116:636-644.

Miura, S., C. Q. Li, Z. Cao, H. Wang, M. R. Wardell, and J. E. Sadler. 2000. Interaction of von Willebrand Factor domain A1 with platelet glycoprotein Ibalpha-(1-289). Slow intrinsic binding kinetics mediate rapid platelet adhesion. *J Biol Chem.* 275:7539-7546.

Nieswandt, B., W. Bergmeier, K. Rackebrandt, J. E. Gessner, and H. Zirngibl. 2000. Identification of critical antigen-specific mechanisms in the development of immune thrombocytopenic purpura in mice. *Blood.* 96:2520-2527.

Norol, F., N. Vitrat, E. Cramer, J. Guichard, S. A. Burstein, W. Vainchenker, and N. Debili. 1998. Effects of Cytokines on Platelet Production From Blood and Marrow CD34+ Cells. *Blood.* 91:830-843.

Nurden, A. T. 2005. Qualitative disorders of platelets and megakaryocytes. *J Thromb Haemost.* 3:1773-1782.

Pai, M., and C. P. Hayward. 2009. Diagnostic assessment of platelet disorders: what are the challenges to standardization? *Semin Thromb Hemost.* 35:131-8.

Patel, S. R., J. H. Hartwig, and J. E. Italiano, Jr. 2005a. The biogenesis of platelets from megakaryocyte proplatelets. *J. Clin. Invest.* 115:3348-3354.

Patel, S. R., J. L. Richardson, H. Schulze, E. Kahle, N. Galjart, K. Drabek, R. A. Shivdasani, J. H. Hartwig, and J. E. Italiano, Jr. 2005b. Differential roles of microtubule assembly and sliding in proplatelet formation by megakaryocytes. *Blood.* 106:4076-4085.

Pedersen, N. T. 1978. Occurrence of megakaryocytes in various vessels and their retention in the pulmonary capillaries in man. *Scand J Haematol.* 21:369-75.

Richardson, J. L., R. A. Shivdasani, C. Boers, J. H. Hartwig, and J. E. Italiano, Jr. 2005. Mechanisms of organelle transport and capture along proplatelets during platelet production. *Blood.* 106:4066-4075.

Robinson, A. J., D. Kashanin, F. O'Dowd, V. Williams, and G. M. Walsh. 2008. Montelukast inhibition of resting and GM-CSF-stimulated eosinophil adhesion to VCAM-1 under flow conditions appears independent of cysLT(1)R antagonism. *J Leukoc Biol.* 83:1522-9.

Rondaij, M. G., R. Bierings, A. Kragt, J. A. van Mourik, and J. Voorberg. 2006. Dynamics and Plasticity of Weibel-Palade Bodies in Endothelial Cells. *Arterioscler Thromb Vasc Biol.* 26:1002-1007.

Ruggeri, Z. M. 2003. Von Willebrand factor, platelets and endothelial cell interactions. *J Thromb Haemost.* 1:1335-42.

Tavassoli, M., and M. Aoki. 1981. Migration of entire megakaryocytes through the marrow—blood barrier. *Br J Haematol.* 48:25-9.

Williams, V., D. Kashanin, I. V. Shvets, S. Mitchell, Y. Volkov, and D. Kelleher. 2002. Microfluidic Enabling Platform for Cell-based Assays. *Journal of the Association for Laboratory Automation.* 7:135-141.

The invention claimed is:

1. An ex vivo method for producing platelets, comprising a step of subjecting a suspension of cells comprising mature megakaryocytes to a flow permitting exposure to a shear rate sufficient for platelet generation, on a solid phase coated with Von Willebrand factor (VWF) or a fragment or variant thereof which binds to GPIb thereby forming platelets.

2. A method according to claim 1, wherein said fragment or variant of VWF is selected from the group consisting of the 52/48-kDa tryptic fragment of VWF; Staphylococcus aureus V-8 protease-digested VWF; VWF concentrates for therapeutic use and VWF mutants responsible for type 2N von Willebrand disease.

3. The method according to claim 1, wherein said mature megakaryocytes are exposed to a shear rate of at least 1000 s−1.

4. The method according to claim 1, wherein said cell concentration in the suspension is between 0.5 and $4 \times 10^6$/mL.

5. The method according to claim 1, wherein said cell concentration in the suspension is at least $4 \times 10^6$/mL.

* * * * *